United States Patent [19]

Julia et al.

[11] 4,219,667
[45] Aug. 26, 1980

[54] SULPHONES WITH AN ALCOHOL GROUP AND THEIR ESTERS

[75] Inventors: Marc Julia, Paris; Albert Menet, Rhone, both of France

[73] Assignee: Rhone-Poulenc S.A., Paris, France

[21] Appl. No.: 421,806

[22] Filed: Dec. 5, 1973

[30] Foreign Application Priority Data

Dec. 7, 1972 [FR] France .................. 72.43582
Dec. 22, 1972 [FR] France .................. 72.45993

[51] Int. Cl.³ .................... C07C 67/02; C07C 147/10
[52] U.S. Cl. ...................... 560/254; 568/32
[58] Field of Search ....... 260/488 H, 607 AR, 476 R; 560/254

[56] References Cited

U.S. PATENT DOCUMENTS

| | | | |
|---|---|---|---|
| 2,507,147 | 5/1950 | Dickey et al. | 260/488 H |
| 3,185,743 | 5/1965 | LaCombe et al. | 260/488 H |
| 3,272,856 | 9/1966 | Braunwarth | 260/488 H |

*Primary Examiner*—Delbert R. Phillips
*Attorney, Agent, or Firm*—Stevens, Davis, Miller & Mosher

[57] ABSTRACT

Sulphones of the formula:

$$RSO_2CH_2CX=CYCH_2OR_1$$

where R is alkyl, aralkyl, alkylaryl or aryl, $R_1$ is hydrogen or $-COR_2$ where $R_2$ is hydrogen, alkyl or aryl, and one of X and Y is methyl and the other is hydrogen are useful for converting terpene and carotenoid compounds into the immediately higher isoprenologue, useful as perfumes, foodstuff dyes, and pharmaceuticals.

6 Claims, No Drawings

SULPHONES WITH AN ALCOHOL GROUP AND THEIR ESTERS

The present invention provides, as new compounds, the sulphones of the formula:

$$RSO_2CH_2—CX=CY—CH_2OR_1 \quad \text{I}$$

in which one of X and Y is a methyl radical and the other is a hydrogen atom, R is a substituted or unsubstituted alkyl, aralkyl, alkylaryl or aryl radical, and $R_1$ is a hydrogen atom or $—COR_2$ in which $R_2$ is hydrogen or an alkyl or aryl radical.

These new compounds can be used in organic synthesis. Because of the reactivity of the methylene group which carries the sulphone group, they react, for example, with alkyl halides or with conjugated diolefines. Thus, with an alkyl halide, for example a chloride of the formula QrCl, Qr being a hydrocarbon radical, the reaction leads to a compound of the formula $Qr—CH(SO_2R)—CX=CY—CH_2OR_1$, which, on desulphonation, for example, with an alkali, changes into a compound of the formula $Qr—CH_2—CX=CY—CH_2OR_1$. When it is considered that, in the sulphones of formula I, the chain $—CH_2CX=CY—CH_2—$ is an isoprene chain, the value of the compounds of the invention in the synthesis of terpene and carotenoid compounds can easily be understood, since they make it possible to pass, in a single step, from one terpene compound to the immediately higher isoprenologue. It is thus possible to synthesise terpene alcohols and esters which are of great value as perfumes, foodstuff dyes, or pharmaceuticals. Examples of such compounds are geraniol, nerol, and vitamin A and its esters such as the acetate, propionate, palmitate, benzoate.

The sulphone esters of formula $RSO_2CH_2—CX=CY—CH_2OCOR_2$ can be prepared by reacting a compound of the formula:

$$RSO_2—A$$

with a compound of the formula:

$$B—OCO—R_2$$

where one of A and B is an alkali metal and the other is a radical of formula: $—CH_2CX=CYCH_2Z$ where Z is halogen. In one embodiment of this method, an alkali metal salt of a carboxylic acid $R_2COOH$ is reacted with a halogenated sulphone of the formula $RSO_2CH_2CX=CY—CH_2Z$ in which R, $R_2$, X and Y are as defined above, and Z is halogen, especially chlorine or bromine. This reaction, for which it is possible to employ the two reagents in equimolecular amounts, is preferably carried out with an excess of the alkali metal carboxylate, for example twice the stoichiometric amount. The reaction is preferably carried out in the presence of a diluent which is inert under the reaction conditions, for example a polar solvent which as dimethylformamide, dimethylsulphoxide, hexamethylphosphoramide or the acid $R_2COOH$ corresponding to the carboxylate employed. It then suffices to heat the mixture at the reflux temperature. The metal halide liberated can be separated easily from the sulphone ester which remains in solution in the reaction medium. The carboxylates employed can be alkali metal salts of fatty acids, especially aliphatic acids of up to 4 carbon atoms, such as formic acid, acetic acid, propionic acid, lauric acid and palmitic acid, or of aromatic acids such as benzoic acid.

Another process for the preparation of the sulphone esters consists of reacting an alkali metal sulphinate of the formula $RSO_2M$, in which R is as hereinbefore defined and M is an alkali metal, with a halogenated ester of the formula $ZCH_2—CX=CY—CH_2—OCOR_2$ in which X, Y, Z and $R_2$ are as hereinbefore defined. In this case the reaction is: $RSO_2M+ZCH_2—CX=CY—CH_2OCOR_2\rightarrow RSO_2CH_2—CX=CY—CH_2OCOR_2+MZ$ The reaction can be carried out in a solvent such as methanol or ethanol, by heating the reaction mixture under reflux. It is also accompanied by the formation of a metal halide which can be separated easily from the desired sulphone ester.

The alkali metal sulphinates used can be sodium or potassium methyl sulphinate, phenyl sulphinate, chlorophenyl sulphinate or tolyl sulphinate.

The sulphones with an alcohol group of formula $RSO_2CH_2—CX=CY—CH_2OH$, in which formula R, X and Y are as hereinbefore defined, can be prepared from the sulphone esters by an acid alcoholysis (hydrolysis) treatment. This is carried out with an inorganic acid such as, for example, hydrochloric acid, the alcohol being methanol, ethanol, a propanol or a butanol. The reaction takes place at ambient temperature but can be accelerated by controlled heating. The desired sulphones with an alcohol group are sparingly soluble in certain solvents such as pentane and hexane, from which they can be purified by recrystallisation.

It is also possible to prepare the sulphones with an alcohol group from the halogenated sulphones of formula $RSO_2CH_2—CX=CY—CH_2Z$, which are subjected to an alkaline hydrolysis with an aqueous solution of an alkali metal hydroxide or an alkali metal carbonate.

The halogenated sulphones employed for the preparation of the alcohols and esters of formula I are known products which can be produced by reacting a sulphonyl halide $RSO_2Cl$ with isoprene (Journal of Organic Chemistry, 1970, 35, 4217) or by reacting an alkali metal sulphinate with a 1,4-dichloro-methyl-2-butene, according to British Patent Application No. 5371/73 Specification No. 1,396,626.

The following Examples illustrate the invention.

EXAMPLE 1

20 cm³ of acetic acid, 6.4 g. of 4-phenylsulphonyl-3-methyl-1-chloro-2-butene and 2.2 g. of sodium acetate are introduced, under a nitrogen atmosphere, into a 100 cm³ 3-necked flask equipped with a mechanical stirrer and a reflux condenser. The mixture is heated under reflux (120° C.) for 2 hours 45 minutes and then left to cool to ambient temperature. The precipitate of sodium chloride formed during the reaction is filtered off and the acetic acid is removed from the filtrate by evaporation in vacuo. The product thus obtained is taken up in 200 cm³ of benzene and the solution obtained is washed with water until neutral. After removing the benzene, the product isolated is washed with distilled water, dried over magnesium sulphate, and recrystallised from absolute ethanol. 5.6 g. of a solid white product, m.p. 95° C., are thus obtained. This product, identified by percentage analysis, infra-red spectrography and nuclear magnetic resonance, is 4-phenylsulphonyl-3-methyl-1-acetoxy-2-butene. Yield: 80%. Degree of conversion of the starting material: 100%.

4-Phenylsulphonyl-3-methyl-1-chloro-2-butene was prepared from isoprene and phenylsulphonyl chloride in accordance with the process described in Journal of Organic Chemistry, 1970, 35, 4217.

EXAMPLE 2

Following the procedure of the preceding Example, 21.7 g. of 4-phenylsulphonyl-2-methyl-1-chloro-butene are reacted with 14 g. of sodium acetate in 100 cm$^3$ of acetic acid. During the heating, the reaction mixture becomes light maroon and the sodium chloride formed precipitates. After heating under reflux for 4 hours, the mixture is allowed to cool to ambient temperature. The product is then taken up in 200 cm$^3$ of water and extracted with 200 cm$^3$ of benzene. The benzene layer is isolated and washed with a 5% aqueous solution of sodium bicarbonate until the pH is 7, and is then dried over sodium sulphate, filtered and concentrated by evaporating the benzene. On treating the residue as described in the preceding Example, 4-phenylsulphonyl-2-methyl-1-acetoxy-2-butene, m.p. 78° C., is isolated and identified.

4-Phenylsulphonyl-2-methyl-1-chloro-2-butene was prepared by reacting sodium phenylsulphinate with 1,4-dichloro-2-methyl-2-butene in anhydrous ethanol, in accordance with the process described in British Patent Application No. 5371/73.

EXAMPLE 3

A mixture of 50.85 g. of sodium phenylsulphinate and 54.1 g. of 4-chloro-3-methyl-1-acetoxy-2-butene in 300 cm$^3$ of ethanol is heated under reflux for 3 hours, under a nitrogen atmosphere, and then filtered hot. The filtrate is cooled on an ice bath and a white precipitate then forms which is filtered off and dried in vacuo. 41.5 g. of a white crystalline product, m.p. 95° C., which is 4-phenylsulphonyl-3-methyl-1-acetoxy-2-butene, are thus obtained. Yield: 60%.

4-Chloro-3-methyl-1-acetoxy-2-butene was prepared by the process described in Journal of American Chemical Society, 1950, 72, 4612.

EXAMPLE 4

48.9 g. of 4-phenylsulphonyl-3-methyl-1-chloro-2-butene, 25 g. of sodium formate and 200 cm$^3$ of 98% formic acid are mixed and the mixture is then heated under a nitrogen atmosphere for 2 hours at 120° C. A white precipitate forms during the reaction. After cooling, the reaction mixture is poured into a liter of iced water, and the white precipitate is filtered off and washed with water until neutral.

Identification carried out on an aliquot portion of this precipitate, by elementary analysis and nuclear magnetic resonance, indicates that it is 4-phenylsulphonyl-3-methyl-1-formyloxy-2-butene.

The moist formate is dissolved in 250 cm$^3$ of methanol containing 5 cm$^3$ of concentrated hydrochloric acid. The solution is stirred at ambient temperature under a nitrogen atmosphere overnight. The methanol is removed by evaporation in vacuo, the residue is dissolved in 300 cm$^3$ of methylene chloride, and this solution is washed with water until neutral and then dried over magnesium sulphate. Evaporation in vacuo of the methylene chloride leaves an oily product from which there is isolated, by recrystallisation from 100 cm$^3$ of pentane at −40° C., filtration and drying, a solid product, m.p. 55° C., identified by percentage analysis and nuclear magnetic resonance as 4-phenylsulphonyl-3-methyl-but-2-en-1-ol. Yield 85% based on the chlorosulphone employed.

This product is dissolved in tetrahydrofuran, cooled to −70° C., and treated with a solution of butyl-lithium in hexane. Isoprene hydrochloride is added and the mixture is left to react for 2 hours at ambient temperature. A sulphone is obtained which is identified as 4-phenylsulphonyl-3,7-dimethyl-octa-2,6-dien-1-ol. Reduction of this sulphone with sodium amalgam, in an alkaline medium, gives a mixture of ocimene and nerol.

We claim:

1. A compound of the formula:

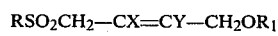

in which one of X and Y is methyl and the other is hydrogen, R is phenyl, and R$_1$ is hydrogen or —COR$_2$ in which R$_2$ is hydrogen, alkyl or phenyl.

2. A compound as claimed in claim 1 which is 4-phenylsulphonyl-3-methyl-1-acetoxy-2-butene.

3. A compound as claimed in claim 1 which is 4-phenylsulphonyl-2-methyl-1-acetoxy-2-butene.

4. A compound as claimed in claim 1 which is 4-phenylsulphonyl-3-methyl-1-formyloxy-2-butene.

5. A compound as claimed in claim 1 which is 4-phenylsulphonyl-3-methyl-but-2-en-1-ol.

6. The compound of the formula:

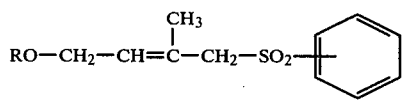

wherein R is H or lower alkanoyl.